United States Patent [19]

Bradshaw et al.

[11] 4,144,393

[45] * Mar. 13, 1979

[54] 3-ACETOXYMETHYL CEPHALOSPORINS HAVING AT POSITION-7 A CARBOXY SUBSTITUTED α-ETHERIFIED HYDROXYIMINOARYLACETAMIDO GROUP

[75] Inventors: Janice Bradshaw, Harrow; Martin C. Cook, Liverpool; Gordon I. Gregory, Chalfont St. Peter, all of England

[73] Assignee: Glaxo Laboratories Limited, Greenford, England

[ * ] Notice: The portion of the term of this patent subsequent to Dec. 20, 1994, has been disclaimed.

[21] Appl. No.: 668,245

[22] Filed: Mar. 18, 1976

Related U.S. Application Data

[63] Continuation-in-part of Ser. No. 533,451, Dec. 16, 1974, abandoned.

[30] Foreign Application Priority Data

Dec. 21, 1973 [GB] United Kingdom ............... 59517/73

[51] Int. Cl.² ................. C07D 501/34; A61K 31/545
[52] U.S. Cl. .......................................... 544/28; 544/30; 424/246
[58] Field of Search ............... 260/243 C; 544/28, 30, 544/29

[56] References Cited

FOREIGN PATENT DOCUMENTS 806450  4/1974  Belgium.
2204060  8/1972  Fed. Rep. of Germany.
2223375  11/1972  Fed. Rep. of Germany.
2262500  7/1973  Fed. Rep. of Germany.
2460537  7/1975  Fed. Rep. of Germany.
68680  1/1974  Luxembourg.

Primary Examiner—Donald G. Daus
Assistant Examiner—D. G. Rivers
Attorney, Agent, or Firm—Bacon & Thomas

[57] ABSTRACT

3-Acetoxymethyl cephalosporin antibiotics in which the 7β-acylamido group has the structure

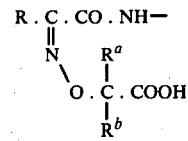

where R is thienyl, furyl or phenyl; $R^a$ is $C_{1-4}$ alkyl, $C_{2-4}$ alkenyl, $C_{3-7}$ cycloalkyl or phenyl, and $R^b$ is hydrogen, carboxy, $C_2$-$C_5$ carbalkoxy or any of the groups designated for $R^a$, or $R^a$ and $R^b$ together with the carbon atom to which they are attached form a $C_{3-7}$ cycloalkylidene or cycloalkenylidene group; exhibit broad spectrum antibiotic activity characterized by particularly high activity against gram negative microorganisms, including those which produce β-lactamases. The compounds, which are syn isomers or exist as mixtures of syn and anti isomers containing at least 90% of the syn isomer, have particularly high in vitro activity against strains of *Escherichia coli, Haemophilus influenzae* and *Proteus* organisms; and also shown unusually high activity against *Pseudomonas* organisms.

8 Claims, No Drawings

3-ACETOXYMETHYL CEPHALOSPORINS HAVING AT POSITION-7 A CARBOXY SUBSTITUTED α-ETHERIFIED HYDROXYIMINOARYLACETAMIDO GROUP

CROSS REFERENCE TO RELATED APPLICATION

This application is a continuation-in-part of our U.S. Application Ser. No. 533,451 filed Dec. 16, 1974, now abandoned.

This invention is concerned with improvements in or relating to cephalosporin compounds, and is more particularly concerned with a novel class of cephalosporin compounds possessing valuable antibiotic properties.

The cephalosporin compounds in this specification are named with reference to "cepham" after *J.Amer.- Chem. Soc.*, 1962, 84, 3400, the term "cephem" referring to the basic cepham structure with one double bond.

Cephalosporin antibiotics are widely used in the treatment of diseases caused by pathogenic bacteria in human beings and animals, for example in the treatment of diseases caused by bacteria which are resistant to other antibiotics such as penicillin compounds, and in the treatment of penicillin-sensitive patients. In many instances it is desirable to employ a cephalosporin antibiotic which exhibits activity against both gram positive and gram negative microorganisms, and a significant amount of research has been directed to the development of various types of broad spectrum cephalosporin antibiotics.

Considerable interest is currently being directed to the development of broad spectrum cephalosporin antibiotics which possess high activity against gram negative organisms. Existing commercially available β-lactam antibiotics tend to exhibit comparatively low activity against certain gram negative organisms such as Proteus organisms, which are an increasingly common source of infection in humans, and are also generally substantially inactive against Pseudomonas organisms. Several Psuedomonas organisms are resistant to the majority of existing commercially available antibiotic compounds, and the practical therapeutic applications of aminoglycoside antibiotics such as gentamicin which do exhibit pseudomonas activity tend to be limited or complicated by the high toxicity of these antibiotics. It is well known that cephalosporin antibiotics normally exhibit low toxicity in man, so that the development of broad spectrum cephalosporin antibiotics possessing high activity against gram negative organisms such as strains of Proteus and Pseudomonas fulfils a significant need in chemotherapy.

The present invention provides novel 7β-acylamidoceph-3-em-4-carboxylic acid antibiotics and non-toxic derivatives thereof. These antibiotics have the formula:

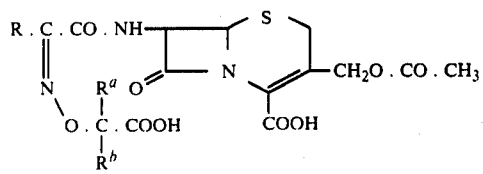

wherein
R is thienyl, furyl or phenyl, $R^a$ is $C_1$-$C_4$ alkyl (e.g. methyl, ethyl, n-propyl, isopropyl or butyl) $C_2$-$C_4$ alkenyl (e.g. vinyl or allyl) $C_3$-$C_7$ cycloalkyl (e.g. cyclopropyl cyclobutyl, cyclopentyl or cyclohexyl) or phenyl;

$R^b$ is hydrogen, carboxy, $C_2$-$C_5$ carbalkoxy (e.g. ethoxycarbonyl) $C_1$-$C_4$ alkyl (e.g. methyl, ethyl, n-propyl, isopropyl or butyl) $C_2$-$C_4$ alkenyl (e.g. vinyl or allyl) $C_3$-$C_7$ cycloalkyl (e.g. cyclopropyl cyclobutyl, cyclopentyl or cyclohexyl) or phenyl;

or $R^a$ and $R^b$ together with the carbon atom to where they are attached form a $C_3$-$C_7$ cycloalkylindene or cycloalkenylidene group (e.g. a cyclobutylidene, cyclopentylidene or cyclohexylidene group).

The compounds are syn isomers or exist as mixtures of syn and anti isomers containing at least 90% of the syn isomer.

These compounds exhibit broad spectrum antibiotic activity characterised by particularly high activity against gram negative microorganisms, including those which produce β-lactamases, and also possess very high stability to β-lactamases produced by a range of gram negative organisms. A characteristic feature of the compounds is their high in vitro activity against gram-negative organisms such as *Enterobacter clocae*, *Serratia marcescens* and *Klebsiella aerogenes*. The compounds have particularly high activity against strains of *Escherichia coli*, *Haemophilus influenzae* and Proteus organism, e.g. strains of *Proteus morganii* and *Proteus mirabilis* and usually high activity against Pseudomonas organisms, for example strains of *Psuedomonas aeruginosa*.

The compounds of the invention are defined as having the syn isomeric form as regards the configuration of the group

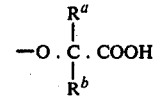

with respect to the carboxamido group. In this specification the syn configuration is denoted structurally as

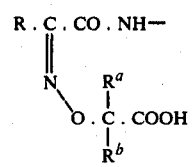

this configuration being assigned on the basis of the work of Ahmad and Spenser reported in *Can. J. Chem.*, 1961, 39 1340. As indicated above, the compounds may exist as mixtures of syn and anti isomers provided that such mixtures contain at least 90% of the syn isomer. We prefer, however, the compounds to be syn isomers essentially free from the corresponding anti isomer.

By "non-toxic derivatives" is meant those derivatives which are physiologically acceptable in the dosage at which they are administered. Such derivatives may include, for example, salts, biologically acceptable esters, 1-oxides and solvates (especially hydrates). It will be appreciated that derivatives such as salts and esters may be formed by reaction of either or both of the carboxyl groups present in the compounds of formula I.

Non-toxic salt derivatives which may be formed from the compounds of general formula I include inorganic base salts such as alkali metal salts (e.g. sodium and potassium salts) and alkaline earth metal salts (e.g. calcium salts); organic base salts (e.g. procaine, phenylethylbenzylamine, dibenzylethylenediamine, ethanolamine, diethanolamine, triethanolamine and N-methylglucosamine salts); and, where appropriate, acid addition salts, e.g. with hydrochloric, hydrobromic, sulphuric, nitric, phosphoric, trifluoroacetic, tolune-p-sulphonic and methane sulphonic acids. The salts may also be in the form of resinates formed with, for example, a polystrene resin or cross-linked polystyrene divinylbenzene copolymer resin containing amino or quaternary amino groups, or, where appropriate, sulphonic acid groups, or, again where appropriate, with a resin containing carboxyl groups, e.g. a polyacrylic acid resin. Use of highly soluble base salts (e.g. alkali metal salts such as the sodium salt) of compounds of formula I is generally advantageous in therapeutic applications because of the rapid distribution of such salts in the body upon administration. Where, however, insoluble salts of compounds (I) are desired in a particular application, e.g. for use in depot preparations, such salts may be formed in conventional manner, for example with appropriate organic amines.

Biologically acceptable, metabolically labile ester derivatives which may be formed from compounds of formula I include, for example, acyloxymethyl esters, e.g. lower alkanoyloxymethyl esters such as acetoxymethyl or pivaloyloxymethyl esters.

Where the group R in the above formulae is a furyl group it may be fur-2-yl or fur-3-yl and where it is a thienyl group it may be thien-2-yl or thien-3-yl.

It will be appreciated that when $R^a$ and $R^b$ in the above formulae are different, the carbon atom to which they are attached may comprise a centre of asymmetry; compounds in accordance with the invention wherein $R^a$ and $R^b$ are different may thus be diastereoisomeric. The invention embraces the individual diastereoisomers of such compounds as well as mixtures thereof.

The term "lower" as used in this specification and the accompanying claims to qualify aliphatic groups denotes, unless otherwise stated, that the said group may contain up to 6 carbon atoms. "Lower" as used to qualify cycloaliphatic groups indicated that the group may contain 3–7 (e.g. 5–7) carbon atoms.

A particularly interesting class of cephalosporin antibiotics in accordance with the invention comprises compounds of general formula

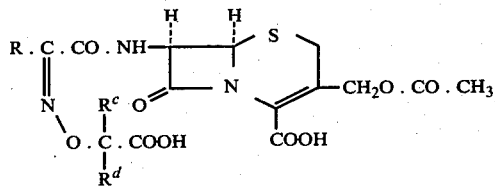

[wherein R is thienyl or furyl, $R^c$ represents methyl, ethyl, propyl, allyl or phenyl and $R^d$ represents hydrogen, carboxy or, more preferably, a group as defined for $R^c$; or $R^c$ and $R^d$ together with the carbon atom to which they are attached form a cyclobutylidene, cyclopentylidene or cyclohexylidene group; and non-toxic derivatives thereof.

These compounds exhibit broad spectrum antibiotic activity (including very high activity against strains of *Haemophilus influenzae* and Proteus organisms) and high β-lactamase stability and are further characterised by particularly high in vitro activity against Pseudomonas organisms such as strains of *Pseudomonas aeruginosa*.

Especially preferred compounds of the above type, by virtue of their particularly high levels of activity against Proteus and Pseudomonas organisms, include the following:

(6R,7R)-3-acetoxymethyl-7-[2-(1-carboxycyclopent-1-yloxyimino)-2-(fur-2-yl)acetamido]ceph-3-em-4-carboxylic acid (syn isomer), (6R,7R)-3-acetoxymethyl-7-[2-(1-carboxybut-3-enyloxyimino)-2-(fur-2-yl)acetamido]ceph-3-em-4-carboxylic acid (syn isomer), (6R,7R)-3-acetoxymethyl-7-[2-(1-carboxycyclobut-1-yloxyimino)-2-(fur-2-yl)acetamido]ceph-3-em-4-carboxylic acid (syn isomer), (6R,7R)-3-acetoxymethyl-7-[2-(1-carboxypropoxyimino)-2-(fur-2-yl)acetamido]ceph-3-em-4-carboxylic acid (syn isomer), (6R,7R)-3-acetoxymethyl-7-[2-(3-carboxypent-3-yloxyimino)-2-(fur-2-yl)-acetamido]ceph-3-em-4-carboxylic acid (syn isomer), (6R,7R)-3-acetoxymethyl-7-[2-(2-carboxyprop-2-yloxyimino)-2-(thien-2-yl)acetamido]ceph-3-em-4-carboxylic acid (syn isomer), and non-toxic derivatives thereof, e.g. alkali metal salts such as the sodium or potassium salts.

The components according to the invention may be prepared by any convenient method, for example by techniques analogous to those described in Belgian Pat. No. 783449.

Thus according to one embodiment of the invention we provide a process for the preparation of an antibiotic compound of general formula I as hereinbefore defined or a non-toxic derivative thereof which comprises either (A) condensing a compound of the formula

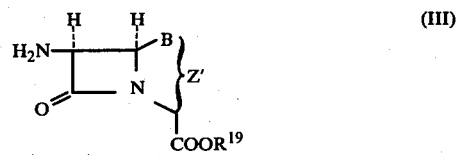

wherein B is >S or >S→O (α− or β−); $R^{19}$ represents hydrogen or a carboxyl blocking group, e.g. the residue of an ester-forming aliphatic or araliphatic alcohol or an ester-forming phenol, silanol or stannanol (the said alcohol, phenol, silanol or stannanol preferably containing 1–20 carbon atoms) or a symmetrical or mixed anhydride group derived from an appropriate acid; and Z' is a group in which 2 carbon atoms link the nuclear sulphur atom and the 4-position carbon atom so that the compound possesses $\Delta^2$ or $\Delta^3$ unsaturation] or a salt, e.g. an acid addition salt such as a hydrochloride, hydrobromide, sulphate, nitrate, phosphate, methane sulphonate or tosylate, or an N-silylated derivative thereof with an acylating agent corresponding to an acid of formula

(wherein R,$R^a$ and $R^b$ are as hereinbefore defined and $R^{20}$ is a carboxyl blocking group, e.g. a group as hereinbefore defined in connection with $R^{19}$); or (B), reacting a compound of the formula

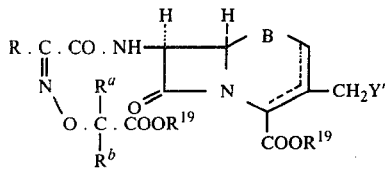

(V)

(wherein B,R,$R^a$ and $R^b$ are as hereinbefore defined; each $R^{19}$ may independently represent hydrogen or a carboxyl blocking group; Y' is a replaceable residue of a nucleophile, e.g. a hydroxy group, a halogen atom such as chlorine, bromine or iodine; and the dotted line bridging the 2-, 3- and 4-positions indicates that the compound is a ceph-2-em or ceph-3-em compound) with a nucleophile e.g. sodium acetate; whereafter, if necessary and/or desired in each instance, any of the following reactions (C) in any appropriate sequence, are carried out:

(i) conversion of a $\Delta^2$ isomer into the desired $\Delta^3$ isomer,
(ii) reduction of a compound wherein B is $>S\to O$ to form a compound wherein B is $>S$,
(iii) acylation of a 3-hydroxymethyl compound to form a 3-acetoxymethyl compound,
(iv) removal of carboxyl blocking groups;
and finally (D) recovering the desired compound of formula I or a non-toxic derivative thereof, if necessary after separation of isomers.

Non-toxic derivatives of the compounds of formula I may be formed in any convenient way, for example according to methods well known in the art. Thus, for example, base salts may be formed by reaction of the cephalosporin acid with sodium 2-ethylhexanoate or potassium 2-ethylhexanoate. Biologically acceptable ester derivatives may be formed using conventional esterifying agents. 1-Oxides may be formed by treatment of the corresponding cephalosporin sulphide with an appropriate oxidising agent, for example with a peracid such as metaperiodic acid, peracetic acid, monoperphthalic acid or m-chloroperbenzoic acid, or with t-butyl hypochlorite, this last reagent conveniently being employed in the presence of a weak base such as pyridine.

Acylating agents which may be employed in the preparation of compounds of formula I include acid halides, particularly acid chlorides or bromides. Such acylating agents may be prepared by reacting an acid (IV) or a salt thereof with a halogenating agent e.g. phosphorus pentachloride, thionyl chloride or oxalyl chloride. Treatment of the sodium, potassium or triethylammonium salt of the acid (IV) with oxalyl chloride is advantageous in that under these conditions isomerisation is minimal.

Acylations employing acid halides may be effected in aqueous and non-aqueous reaction media, conveniently at temperatures of from $-50°$ to $+50°$ C., preferably $-20°$ to $+30°$ C., if desired in the presence of an acid binding agent. Suitable reaction media include aqueous ketones such as aqueous acetone, esters such as ethyl acetate, halogenated hydrocarbons, such as methylene chloride, amides such as dimethylacetamide, nitriles such as acetonitrile, or mixtures of two or more such solvents. Suitable acid binding agents include tertiary amines (e.g. triethylamine or dimethylaniline), inorganic bases (e.g. calcium carbonate or sodium bicarbonate), and oxiranes such as lower 1,2-alkylene oxides (e.g. ethylene oxide or propylene oxide) which bind hydrogen halide liberated in the acylation reaction.

Acids of formula IV may themselves be used as acylating agents in the preparation of compounds of formula I. Acylations employing acids(IV) are desirably conducted in the presence of a condensation agent, for example, a carbodiimide such as N,N'-diethyl-, dipropyl- or diisopropylcarbodiimide, N,N'-dicyclohexylcarbodiimide or N-ethyl-N'-γ-dimethylaminopropylcarbodiimide; a carbonyl compound such as carbonyldiimidazole; or an isoxazolinium salt such as N-ethyl-5-phenylisoxazolinium perchlorate. Acylation reactions of this type are desirably effected in an anhydrous reaction medium, e.g. methylene chloride, dimethylformamide or acetonitrile.

Acylation may also be effected with other amide-forming derivatives of acids of formula IV such as, for example, a symmetrical anhydride or a mixed anhydride (e.g. with pivalic acid or formed with a haloformate such as a lower alkylhaloformate). The mixed or symmetrical anhydride may be generated in situ; thus, for example, a mixed anhydride may be generated using N-ethoxycarbonyl-2-ethoxy-1,2-dihydroquinoline.

Mixed anhydrides may also be formed with phosphorus acids (for example phosphoric or phosphorous acids), sulphuric acid or aliphatic or aromatic sulphonic acids (for example p-toluene sulphonic acid).

It will be appreciated that in processes for the preparation of compounds of formula I wherein $R^b$ represents carboxy it will in many instances be necessary to protect the carboxy group, for example by substitution with a carboxyl blocking group, e.g. a group as hereinbefore defined in connection with $R^{19}$.

Any transformations of substituents at the 3-position which may be necessary in the preparation of particular compounds of formula I may, for example, be effected by methods described in the literature.

$\Delta^2$-Cephalosporin ester derivatives obtained in accordance with the process of the invention may be converted into the corresponding $\Delta^3$ derivative by, for example, treatment of the $\Delta^2$ ester with a base.

Ceph-2-em reaction products may also be oxidised to yield the corresponding ceph-3-em 1-oxide, for example by reaction with a peracid as mentioned previously; the resulting sulphoxide may, if desired, subsequently be reduced as described hereinafter to yield the corresponding ceph-3-em sulphide.

Where a compound is obtained in which B is $>S\to O$ this may be converted to the corresponding sulphide by, for example, reduction of the corresponding acyloxysulphonium or alkyloxysulphonium salt prepared in situ by reaction with e.g. acetyl chloride in the case of an acetoxysulphonium salt, reduction being effected by, for example, sodium dithionite or by iodide ion as in a solution of potassium iodide in a water miscible solvent e.g. acetic acid, tetrahydrofuran, dioxan, dimethylformamide or dimethylacetamide. The reaction may be effected at a temperature of $-20°$ to $+50°$ C.

Where a compound of formula I is obtained as a mixture of isomers, the syn isomer may be obtained by, for example, conventional methods such as crystallization or chromatography, Syn and anti isomers may be distinguished by appropriate techniques, e.g. by their ultraviolet spectra, by thin layer or paper chromatography or by their proton magnetic resonance spectra. Thus, for example, the p.m.r. spectra of DMSO-d$_6$ solutions of syn compounds of Formula I exhibit the doublet for the amide NH at a lower field than do similar solutions of the corresponding anti-isomers. These factors may be employed in monitoring reactions.

Acids (IV) may be obtained by reacting a glyoxylic acid of formula $$R.CO.COOH \quad (VI)$$

(where R has the above-defined meaning) or an ester thereof with a hydroxylamine derivative of formula

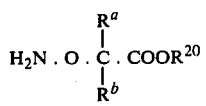
(VII)

(where $R^a$, $R^b$ and $R^{20}$ have the above-defined meanings). The resulting acid or ester may be separated into its syn and anti isomers by, for example, crystallisation, chromatography or distillation, whereafter ester derivatives may be hydrolysed to yield the corresponding acid.

Acids (IV) may also be prepared by etherification of an acid of formula

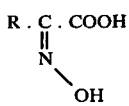
(VIII)

(where R has the above-defined meaning), e.g. by reaction with a compound of general formula

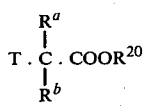
(IX)

(wherein $R^a$, $R^b$ and $R^{20}$, are as hereinbefore defined and T is halogen such as chloro, bromo or iodo; sulphate; or sulphonate such as tosylate). Separation of isomers may be effected either before or after such etherification. The etherification reaction is desirably carried out in the presence of a base, e.g. potassium t-butoxide or sodium hydride, and is preferably conducted in an organic solvent, for example dimethylsulphoxide, a cyclic ether such as tetrahydrofuran or dioxan, or an N,N-disubstituted amide such as dimethylformamide. Under these conditions the configuration of the oximino group is substantially unchanged by the etherification reaction.

Acids of formula IV and acylating agents derived therefrom (e.g. acyl halides such as the chloride) are novel and comprise a feature of the present invention.

Derivatives of the compounds of the invention in which the carboxy substituent of the 7β-acylamido side chain is substituted by a carboxyl blocking group are also new and comprise a feature of the invention. These monoester derivatives, which may be represented by the general formula

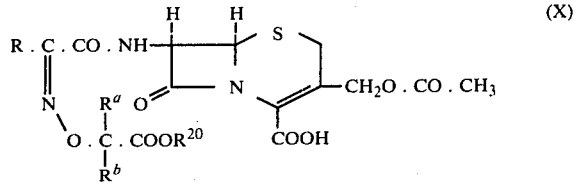

(wherein R, $R^a$ and $R^b$ are as hereinbefore defined and $R^{20}$ is a carboxyl blocking group such as t-butyl or diphenylmethyl), are of value as intermediates in the preparation of antibiotic compounds of general formula I. The compounds (X) may themselves exhibit antibiotic activity, although generally at a very low level when compared to corresponding compounds (I).

Carboxyl blocking groups $R^{20}$ and, where appropriate, $R^{19}$ used in the preparation of compounds of formula I or in the preparation of necessary starting materials are desirably groups which may readily be split off at a suitable stage in the reaction sequence, conveniently as the last stage. It may, however, be convenient in some instances to employ biologically acceptable, metabolically labile carboxyl blocking groups such as acyloxymethyl groups (e.g. pivaloyloxymethyl) and retain these in the final product to give a biologically acceptable ester derivative of a compound of formula I.

Suitable carboxyl blocking groups are well known in the art, a list of representative blocked carboxyl groups being included in Belgian Pat. No. 783,449. Preferred blocked carboxyl groups include aryl lower alkoxycarbonyl groups such as p-methoxybenzyloxycarbonyl, p-nitrobenzyloxycarbonyl and diphenylmethoxycarbonyl; lower alkoxycarbonyl groups such as t-butoxycarbonyl; and lower haloalkoxycarbonyl groups such as 2,2,2-trichloroethoxycarbonyl. The carboxyl blocking group may subsequently be removed by any of the appropriate methods disclosed in the literature; thus, for example, acid or base catalysed hydrolysis is applicable in many cases, as are enzymically-catalysed hydrolyses.

The antibiotic compounds of the invention, e.g. compounds of formula I and non-toxic derivatives thereof, may be formulated for administration in any convenient way, by analogy with other antibiotics and the invention therefore includes within its scope pharmaceutical compositions comprising an antibiotic compound in accordance with the invention adapted for use in human or veterinary medicine. Such compositions may be presented for use in conventional manner with the aid of any necessary pharmaceutical carriers or excipients.

The antibiotic compounds according to the invention may be formulated for injection and may be presented in unit dose form in ampoules, or in multi-dose containers with an added preservative. The compositions may take such forms as suspensions, solutions, or emulsions in oily or aqueous vehicles, and may contain formulatory agents such as suspending, stabilising and/or dispersing agents. Alternatively the active ingredient may be in powder form for reconstitution with a suitable vehicle, e.g. sterile, pyrogen-free water, before use.

The antibiotic compounds may also be presented in a form suitable for absorption by the gastro-intestinal tract. Tablets and capsules for oral administration may be in unit dose presentation form, and may contain conventional excipients such as binding agents, for example syrup, acacia, gelatin, sorbitol, tragacanth or polyvinylpyrrolidone; fillers, for example lactose, sugar, maize-starch, calcium phosphate, sorbitol or glycine; lubricants, for example magnesium stearate, talc, polyethylene glycol or silica; disintegrants, for example potato starch; or acceptable wetting agents such as sodium lauryl sulphate. The tablets may be coated according to methods well known in the art. Oral liquid preparation may be in the form of, for example, aqueous or oily suspensions, solutions, emulsions, syrups or elixirs, or may be presented as a dry product for reconstitution with water or other suitable vehicle before use. Such liquid preparation may contain conventional additives such as suspending agents, for example sorbitol syrup, methyl cellulose, glucose/sugar syrup, gelatin, hydroxyethylcellulose, carboxymethyl cellulose, aluminium stearate gel or hydrogenated edible fats; emulsifying agents, for example lecithin, sorbitan mono-oleate or acacia; non-aqueous vehicles (which may include edible oils), for example almond oil, fractionated coconut oil, oily esters, propylene glycol or ethyl alcohol; and preservatives, for example methyl or propyl p-hydroxybenzoates or sorbic acid. The antibiotic compounds may also be formulated as suppositories, e.g. containing conventional suppository bases such as cocoa butter or other glyceride.

Compositions for veterinary medicine may, for example, be formulated as intramammary preparations in either long acting or quick-release bases.

The compositions may contain from 0.1% upwards, e.g. 0.1–99%, preferably from 10–60% of the active material, depending on the method of administration. When the compositions comprise dosage units, each unit will preferably contain 50–1500 mg of the active ingredient. The dosage as employed for adult human treatment will preferably range from 500 to 5000 mg per day, depending on the route and frequency of administration, although in treating Pseudomonas infections higher daily doses may be required.

The antibiotic compounds according to the invention may be administered in combination with other therapeutic agents such as antibiotics, for example penicillins, tetracyclines or other cephalosporins.

The following examples illustrate the invention. All temperatures are in ° C. The structure of the products were verified by p.m.r. spectroscopy (Preparations and Examples) and i.r. spectroscopy (Examples only).

Preparation 1

2-(2-t-Butoxycarbonylprop-2-yloxyimino)-2-(fur-2-yl)acetic acid (syn isomer)

A solution of 2-(fur-2-yl)-2-hydroxylminoacetic acid (syn isomer) (14.1 g) in dimethyl sulphoxide (100 ml) was added all at once to a magnetically stirred solution of potassium t-butoxide (22.4 g) in dimethyl sulphoxide (400 ml), the reaction mixture being maintained under an atmosphere of dry nitrogen. A gel was formed which, on stirring, became a finely divided, yellow solid. Stirring was continued for one hour, and then a solution of t-butyl 2-bromo-2-methylpropionate (24.0 g) in dimethyl sulphoxide (50 ml) was added over one hour to the reaction mixture at room temperature. After addition was complete, the resulting solution was stirred for a further hour. The reaction was poured into ice-water (1.5 liters) and acidified under ether (500 ml) to pH 1.8 with concentrated hydrochloric acid. The two layers were separated, and the aqueous layer was extracted with more ether. The combined ether extracts were washed once with water, then extracted with aqueous sodium bicarbonate solution. The combined alkaline extracts were acidified under ether to pH 1.8 with concentrated hydrochloric acid, and the acid solution was extracted further with ether. The combined ether extracts were washed (water, saturated brine), dried, and concentrated to a yellow oil, which crystallised under high vacuum (22.41 g, 83%), $\lambda_{max}$(EtOH) 272.5 nm ($\epsilon$ 15,400).

The above solid (22.4 g) was crystallised from carbon tetrachloride (25 ml) to give the title compound (16.42 g, 61%) m.p. 74.5°–74.2° (73.0°).

Preparations 2–14

Method A

The dipotassium salt of 2-(fur-2-yl)-2-hydroxyiminoacetic acid (syn isomer) was generated under an atmosphere of dry nitrogen and alkylated with the appropriate halo-t-butyl ester as described in Preparation 1. The products were isolated by pouring into water, acidifying, and extracting in the conventional manner.

Method B

As method A but using a halo-diphenylmethyl ester.

The half esters prepared by these methods are listed in Table 1.

TABLE 1

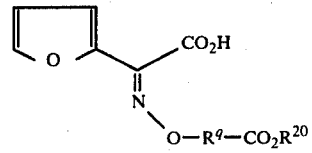

| Preparation No. | $R^q$ | $R^{20}$ | Method | m.p. ° C | $\lambda_{max}$, nm (solvent) | $\epsilon$ | $\lambda$ values for $d_6$-DMSO $R^q$ | $R^{20}$ |
|---|---|---|---|---|---|---|---|---|
| 2 | >CHCH₃* | —C(CH₃)₃ | A | 69.8–73.4° | 277 (pH6 buffer) | 15,500 | 5.31; 8.56 | 8.58 |
| 3 | (cyclopentyl) | " | A | 106.8–107.3° | 277.5 (pH6 buffer) | 15,100 | 8.03;8.30 | 8.63 |
| 4 | >CH(CH₂)₃CH₃* | —CHPh₂ | B | 102–104° | 275 (EtOH) | 12,700 | 5.1;8.16; 8.7;9.18 | 3.07(CH) |

TABLE 1-continued

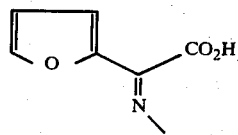

| Preparation No. | R^q | R^20 | Method | m.p. °C | λ_max, nm (solvent) | ε | λ values for d_6-DMSO R^q | R^20 |
|---|---|---|---|---|---|---|---|---|
| 5 | >CHCH₂CH₃* | " | B | — | 271.5 (EtOH) | 14,100 | 5.13;8.11 9.07 | 3.09(CH) |
| 6 | >C(C₂H₅)(C₂H₅) | " | B | — | 269 (EtOH) | 13,200 | 8.08;9.22 | 3.10(CH) |
| 7 | >CH(CH₂)₂CH₃* | " | B | 116–117° | 270 (EtOH) | 14,750 | 5.10;7.9–8.9; 9.1 (d₆-DMSO) | 3.08(CH) |
| 8 | >CH-cyclohexyl* | " | B | — | 270 (EtOH) | 13,400 | 5.32;7.8–9.2 (d₆-DMSO) | 3.07(CH) |
| 9 | >CH—CH(CH₃)₂* | " | B | — | 270.5 266.5 (EtOH) | 13,700 13,250 | 5.14;7.68;8.95 9.15(CDCl₃) | 3.05(CH) |
| 10 | >CH—CH₂CH=CH₂* | —C(CH₃)₃ | A | 77.0–80.3° | 276.5 (pH6 buffer) | 17,500 | 4.26;4.86;4.91 5.38;7.44 (d₆-DMSO) | 8.60 |
| 11 | gem-dimethylcyclohexyl | " | A | 91.5° | 276.5 (pH6 buffer) | 16,700 | 8.12;8.50 (d₆-DMSO) | 8.57 |
| 12 | >C(CH₃)(CO₂C(CH₃)₃) | " | A | 91.5–93.8° | 276 (pH6 buffer) | 15,800 | 8.39;8.56 (d₆-DMSO) | 8.56 |
| 13 | spiro | " | A | 113–114° | 248 (pH6 buffer) | 17,200 | 7.4–8.3 | 8.59 |
| 14 | >C(CH₃)(CO₂C₂H₅)* | " | A | + | — | — | 5.76;8.74;8.33 (CH₃) | 8.54 |

*Denotes (RS)-isomers
+N-benzyl-2-Phenylethylammonium salt mp. 129°

Preparation 15

2-(2-t-Butoxycarbonylprop-2-yloxyimino)-2-(thien-2-yl)acetic acid (syn isomer)

The title compound was prepared from 2-hydroxyimino-2-(thien-2-yl)acetic acid (syn isomer) and t-butyl 2-bromo-2-methylpropionate, in a similar manner to that described for Preparation 1, in 78% yield as a colourless oil, and was characterised as the N-benzyl-2-phenylethylammonium salt, m.p. 201.3°–201.9° (from ethanol).

Preparation 16 t-Butyl 1-Bromocyclopentanecarboxylate

To a mixture of 1-bromocyclopentanecarboxylic acid (36.99 g) and anhydrous ether (35 ml) in a 500 ml pressure bottle, containing a magnetic stirrer-bar, was added concentrated sulphuric acid (3.5 ml), followed by precondensed isobutene (150 ml). The bottle was sealed, and stirred at ambient temperature for 20 hours. The bottle was then opened excess isobutene was evaporated, and the residue in ether was washed with aqueous sodium bicarbonate solution and water, dried, and concentrated. The residue was distilled under reduced pressure to give the title ester (b.p. 66°–74°/0.5–2.0 mm) (33.6 g, 70%); $\lambda_{max}$(CHBr₃) 1702 cm$^{-1}$; τ (CDCl₃) 7.78, 8.20 (cyclopentane protons) and 8.54 (C(CH₃)₃).

Preparation 17

Diphenylmethyl α-bromohexanoate

α-Bromohexanoic acid (1.95 g) in light petroleum spirit (25 ml, b.p. 40°–60°) was treated with a stock solution of diphenyldiazomethane in petroleum spirit (b.p. 40°–60°) (ca. 3.8 mmole/10ml) dropwise with stirring until a faint violet colour persisted. The mixture was stirred for 2 hours at room temperature, whereupon the solvent was removed in vacuo. The resulting oil in ethyl acetate was washed with a saturated aqueous solution of sodium bicarbonate then with water and dried. Removal of the solvent gave the title ester (3.0 g, 90%), $\lambda_{max}$(EtOH) 252, 258, 263.5, 267.5 and 276 nm (ε 1650, 1600, 1350, 1150 and 850).

Preparations 18–25

α-Halo Substituted Carboxylic Acid Esters

Method A

The appropriate α-halo carboxylic acid was treated with isobutene and concentrated sulphuric acid in a pressure bottle at room temperature for 10–40 hours by the method described in Preparation 16 to give the t-butyl esters listed in Table 2.

Method B

The appropriate α-halo carboxylic acid in a solvent (e.g. ether, petroleum, ethyl acetate) was treated with a solution of diphenyldiazomethane until a faint permanent colour was obtained. The ester was washed with alkali in the manner described in Preparation 17 to give the diphenylmethyl esters listed in Table 2.

Preparation 28

2-t-Butoxycarbonylmethoxyimino-2-(fur-2-yl)acetic acid (syn isomer)

The pH of a mixture of fur-2-ylglyoxylic acid (4.2 g), t-butoxycarbonylmethoxyamine (4.5 g) and water (50 ml) was adjusted to 5.0 with 2N sodium hydroxide solution. The resulting solution was stirred for 16 hours. The pH of the solution was increased to 7.0, and the solution was washed twice with ether. The aqueous

TABLE 2

$X-R^q-CO_2R^{20}$

| Preparation No. | X | $R^q$ | $R^{20}$ | Method | Ester $\nu_{max}$cm$^{-1}$ (CHBr$_3$) | τ values (solvent) $R^q$ | $R^{20}$ |
|---|---|---|---|---|---|---|---|
| 18 | Br | \C(CH$_3$)$_2$/ | —C(CH$_3$)$_3$ | A | 1716 | 5.74;8.22 (CDCl$_3$) | 8.51 |
| 19 | Br | \CHCH$_2$CH$_3$*/ | —CHPh$_2$ | B | 1737 | 5.29;7.97;9.07 (d$_6$-DMSO) | 3.10 (CH) |
| 20 | Br | \C(C$_2$H$_5$)$_2$/ | " | B | 1729 | 7.81;9.10 (d$_6$-DMSO) | 3.06 (CH) |
| 21 | Br | \CH(CH$_2$)$_2$CH$_3$*/ | " | B | 1730 | 5.24;7.7-8.9;9.12 (d$_6$-DMSO) | 3.09 (CH) |
| 22 | Br | \CH—C$_6$H$_{11}$*/ | " | B | 1725,1245 | 5.45,7.8-9.3(d$_6$-DMSO) | 3.04 (CH) |
| 23 | Br | \CHCH(CH$_3$)$_2$*/ | " | B | 1738 | 5.40;7.79;9.0;9.08 (d$_6$-DMSO) | 3.10 (CH) |
| 24 | Br | cyclohexyl | —C(CH$_3$)$_3$ | A | 1710 | 7.9;8.0-8.9 | 8.51 |
| 25 | Br | cyclobutyl | " | A | 1714 | 6.9-7.6;7.7-8.3 | 8.52 |

*Denotes (RS)-isomers

Preparation 26

Di-t-butyl 2-Bromo-2-methylmalonate

To a stirred suspension of sodium hydride (1.7 g, 80% dispersion in oil) in tetrahydrofuran (60 ml) under an atmosphere of nitrogen was added di-t-butyl methylmalonate (11.52 g). The mixture was stirred at 60°-70° for 1.5 hours to give a clear solution. This solution was cooled to −25°, and to it was rapidly added a solution of bromine (2.6 ml) in dichloromethane (30 ml). The solution was allowed to warm to ambient temperature, then concentrated. The residue in ether was washed with water, dried, and fractionally distilled under reduced pressure to give the title compound b.p. 78°-86°/1.0 mm Hg, (7.56 g, 49%); $\nu_{max}$(CHBr$_3$) 1730cm$^{-1}$ (CO$_2$-Bu$^t$); τ (CDCl$_3$) values include 8.05 (s, C(CH$_3$)$_3$) and 8.53 (2s, CH$_3$ and C(CH$_3$)$_3$).

Preparation 27 t-Butyl Ethyl 2-Bromo-2-methylmalonate

The title compound was prepared in a similar manner to that used for the dibutyl ester in Preparation 26, in 83% yield, b.p. 64°-68°/0.03 mm Hg.

solution was acidified to pH 1.8 under ether, and further extracted with ether. The combined ether extracts were washed (water, saturated brine), dried, and concentrated to give a solid (7.62 g), which was crystallised from carbon tetrachloride to give the title compound (3.67 g, 46%) m.p. 105.1°-106.2°; $\lambda_{max}$ (pH 6 phosphate buffer) 277.5 nm (ε 16,300).

Preparation 29

2-RS-α-t-Butoxycarbonylbenzyloxyimino-2-(fur-2-yl)acetic acid (syn isomer)

(a)(i) A mixture of N-hydroxyphthalimide (24.5 g), anhydrous potassium carbonate (16.5 g), t-butyl α-bromophenylacetate (41 g) and dimethylsulphoxide (225 ml) was stirred for 18 hours and was then poured into water (1.2 liters). The precipitated solid was filtered off, washed well with water, dried, and crystallised from industrial methylated spirits to give N-[α-(t-butoxycarbonyl) benzyloxy] phthalimide (41 g, 78%); m.p. 120.6°-121.5°.

(ii) To a solution of the above oxyphthalimide (40 g) in dichloromethane (500 ml) was added 100% hydrazine hydrate (11.4 ml). A precipitate was formed immediately. The mixture was stirred for 1.5 hours, whereafter sufficient 5N ammonium hydroxide solution was added to dissolve the precipitate. The two layers were separated, and the aqueous layer was extracted once with methylene chloride. The combined organic extracts were washed (water, saturated brine), dried, and concentrated to give t-butyl α-(aminooxy)phenylacetate (25.0 g, 98%) as colourless crystals, m.p. 48.2°–49.6°.

(b) Fur-2-ylglyoxylic acid and t-butyl α-(aminooxy)phenylacetate were reacted as described in Preparation 1 to yield the title compound in 42% yield, m.p. 97.9°–98.9° (from carbon tetrachloride); $\lambda_{max}$ (pH 6 phosphate buffer) 278 nm ($\epsilon$ 18,400).

Preparation 30 syn-2-(2-tert-Butoxycarbonylprop-2-yloxyimino)-phenylacetic acid.

To a well-stirred solution of potassium tert-butoxide (449 mg, 4 mmole) in dry DMSO (10 ml) was added in one portion a solution of syn-2-hydroxyiminophenylacetic acid (330 mg, 2 mmole) in DMSO (5 ml). The mixture was stirred for 45 min, then tert-butyl α-bromoisobutyrate (446 mg, 2 mmole) in DMSO (5 ml) was added. The mixture was stirred for 3.5 hr at room temperature, then poured into ice-water (150 ml). Ether (125 ml) was added and the pH was adjusted to 1.5 (conc. HCl). the aqueous layer was again extracted with ether, and the ether extracts washed with water and extrcted into saturated sodium bicarbonate solution. The extract was acidified (pH 1.5) and extracted with ether. The ether layer was separated and washed with water and dried ($Na_2SO_4$). Evaporation left an oil, which later solidified. The product was dissolved in methylene chloride (8 ml) and filtered, and the filtrate was evaporated, leaving an off-white solid (310 mg, 50%), m.p. 102°–150°, $\lambda_{max}$ (58994, EtOH) 253.5 nm ($\epsilon$ 12,700).

EXAMPLE 1

(a)

(6R,7R)-3-Acetoxymethyl-7-[2-t-butoxycarbonylmethoxyimino-2-(fur-2-yl)acetamido] ceph-3-em-4-carboxylic acid (syn isomer)

Oxalyl chloride (0.45 ml) was added at 5° to a stirred solution of 2-t-butoxycarbonylmethoxyimino-2-(fur-2-yl)acetic acid (syn isomer) (1.35 g) in dry dichloromethane (50 ml) containing triethylamine (0.7 ml) and dimethylformamide (1 drop). The solution was stirred at 5° for one hour and was then evaporated to dryness at 5°. The residue was suspended in acetone (50 ml) and was added over 30 minutes to a stirred, ice-cooled solution of (6R,7R)-3-acetoxymethyl-7-aminoceph-3-em-4-carboxylic acid (1.36 g) in water (100 ml) and acetone (50 ml) containing sodium bicarbonate (1.0 g). The reaction mixture was stirred for one hour, whereafter the acetone was evaporated under reduced pressure. The residue was acidified to pH 1.8, and this mixture was extracted with ether. The combined extracts were washed (water, saturated brine), dried, and evaporated to give the title compound (2.52 g, 96%) as a pale yellow foam, $[\alpha]_D + 28.5°$ (c 0.96, DMSO); $\lambda_{max}$ (pH 6 phosphate buffer) 276.5 nm ($\epsilon$ 17,900).

(b)

(6R,7R)-3-Acetoxymethyl-7-[2-carboxymethoxyimino-2-(fur-2-yl)-acetamido]ceph-3-em-4-carboxylic acid, disodium salt (syn isomer)

A solution of (6R,7R)-3-acetoxymethyl-7-[2-t-butoxycarbonylmethoyimino-2-(fur-2-yl)acetamido]ceph-3-em-4-carboxylic acid (syn isomer) (1.422 g) and anisole (0.25 ml) in trifluoroacetic acid (5 ml) was kept at ambient temperature for 5 minutes. The mixture was concentated at reduced pressure, ethyl acetate (10 ml) was added, and the mixture was re-evaporated. The residue was distributed between ether and sodium bicarbonate solution. The ether layer was extracted further with sodium bicarbonate solution and the combined alkaline extracts were acidified to pH 1.8 under ether. The acid mixture was extracted with ether, and the combined ether extracts were washed (water, saturated brine), dried, and evaporated to give the dicarboxylic acid corresponding to the title compound (942 mg, 74%), τ ($d_6$ - DMSO) values include 0.24 (d, J 8 Hz, NH), 4.13 (dd, 7-H), and 5.31 (s, $CH_2CO_2H$).

This di-acid (900 mg) in acetone (9 ml) was neutralised with a solution of sodium 2-ethylhexanoate (700 mg) in acetone (5 ml). The mixture was stirred for 10 minutes, then the precipitated solid was filtered off, washed with a little acetone, and dried to give the title compound (807 mg, 60%), $[\alpha]_D + 15°$ (c 1.08, DMSO); $\nu_{max}$ (Nujol) 1766 $cm^{-1}$ (β-lactam).

EXAMPLES 2–18

General Procedure for the Preparation of (6R,7R)-7-(2-Aryl-2-carboxy-$R^q$-oxyiminoacetamido)-3-(substituted) ceph-3-em-4-carboxylic Acids (syn-isomers) and/or their Salts Method A Following the prcedure described in Example 1, a solution of the of the appropriate 2-aryl-2-t-butoxycarbonyl-$R^q$-oxyiminoacetic acid (syn-isomer) (1 equiv) in methylene chloride optionally containing a few drops of N,N-dimethylformamide and triethylamine (1 equiv) was treated with oxalyl chloride (1 equiv) at 0°–5° for ca. 1 hour. The mixture was then evaporated to dryness. The residue was suspended or dissolved in acetone and added to a stirred, ice-cold solution of (6R,7R)-3-acetoxymethyl-7-aminoceph-3-em-4-carboxylic acid (1–1.2 equiv) in water or a mixture of acetone and water containing sodium hydrogen carbonate (2–2.5 equiv). The reaction mixture was stired for 0.5–2.5 hours, allowing the temperature to rise to room temperature, whereafter the acetone was removed under reduced pressure. The pH was adjusted to 1.5–2.0 and the product extracted into ethyl acetate (alternatively ether or methylene chloride may be used). The organic layer was washed with water and/or saturated brine, dried and evaporated to give the corresponding (6R,7R)-3-acetoxymethyl-7-(2-aryl-2-t-butoxycarbonyl-$R^q$-oxyiminoacetamido)ceph-3-em-4-carboxylic acid (syn-isomer) which was characterised by optical rotation and/or by spectroscopy.

The t-butyl esters were deprotected by treating with trifluoroacetic acid containing anisole at room temperature for at least 5 minutes. The reaction mixture was evaporated in vacuo and the product isolated by trituration or by distributing between ethyl acetate (or ether) and an aqueous solution of sodium hydrogen carbonate, separating the aqueous extracts, acidifying these extracts under ethyl acetate and isolating the title dicarboxylic acid in the usual way. The products are listed in Table 3.

Method B

As Method A except that the appropriate 2-aryl-2-diphenylmethoxycarbonyl-$R^q$-oxyiminoacetic acid (syn-isomer) was used in place of the t-butyl ester. The products are listed in Table 3.

Method C

As Method A or B except that the dicarboxylic acid was converted into its disodium salt by treating a solution of the acid in acetone with a solution of sodium 2-ethylhexanoate in acetone. The precipitated disodium salt was washed and dried. The products are listed in Table 3.

TABLE 3

| Ex. No. | $R^p$ | $R^q$ | Salt | Method | $[\alpha]_D$ (DMSO) | $\lambda_{max}$, nm (pH 6 buffer) | $\epsilon$ | β-lactam $\nu_{max}$, cm$^{-1}$ (Nujol) | τ values* for d$_6$-DMSO at 100 MHz x | y | $R^q$ |
|---|---|---|---|---|---|---|---|---|---|---|---|
| 2 | furyl | CHPh** | — | A | +48° | 277.5 | 18,700 | 1778 | 0.13; 0.20 | 4.08; 4.16 | 4.28;4.32(CH) 2.3–2.6(Ph) |
| 3 | furyl | CHCH$_3$** | disodium | A,C | +63° | 275 | 16,800 | 1764 | 0.29 | 4.10 | 5.27(CH) 8.54(CH$_3$) |
| 4 | furyl | C(CH$_3$)$_2$ | disodium | A,C | +95° | 274 | 16,800 | 1768 | 0.32 | 4.05 | 8.47 |
| 5 | furyl | cyclopentyl | disodium | A,C | +62° | 276 | 16,800 | 1756 | 0.38 | 4.10 | 7.90 and 8.28 |
| 6 | furyl | CHCH$_2$CH=CH$_2$** | disodium | | +40° | 276 | 15,400 | 1760 | ~4.15 0.29 | 4.1, 7.38 | ~4.8,5.34, |
| 7 | furyl | cyclohexyl | disodium | A,C | +76.5° | 275 | 15,500 | 1756 | 0.38 | 4.13 | 8.20,8.50 |
| 8 | furyl | C(CO$_2$H)(CH$_3$) | — | A | +43° | 274.5 | 10,100 | 1760 | 0.37 | 4.16 | 8.36 |
| 9 | furyl | cyclobutyl | | A,B | +28° | 274 | 14,600 | 1780 | 0.31 | 4.09 | 7.56,8.08 |
| 10 | furyl | C(CO$_2$Et)(CH$_3$)** | — | A | +21° | 275.5 | 17,200 | 1790 | 0.33 | 4.16 | 5.80,8.33,8.80 |
| 11 | furyl | CH(CH$_2$)$_3$CH$_3$** | — | B | +45° | 274 | 19,150 | 1771 | 0.31 | 4.11 | 5.40;8.2;8.6 9.1 |
| 12 | furyl | CHCH$_2$CH$_3$** | — | B | +57° | 274 | 18,000 | 1776 | | | |
| 13 | furyl | C(C$_2$H$_5$)$_2$ | — | B | +44° | 272.5 | 17,000 | 1773 | 0.41 | 4.16 | 8.1;9.2 |

TABLE 3-continued

Structure shown:
R^p-C(=N-O-R^q)-CONH-[H(x)]-[β-lactam ring with H(y)]-S-CH2-C(=)-CH2O.CO.CH3, with CO2H on the ring nitrogen side.

| Ex. No. | R^p | R^q | Salt | Method | [α]_D (DMSO) | λ_max, nm (pH6 buffer) | ε | β-lactam ν_max, cm⁻¹ (Nujol) | τ values* for d6-DMSO at 100 MHz — x | y | 7.85; 9.0 R^q |
|---|---|---|---|---|---|---|---|---|---|---|---|
| 14 | furan-2-yl | CH(CH2)2CH3** | — | B | +53° | 273 | 16,900 | 1780 | 0.37 | 4.10 | 5.40; 542 |
| 15 | furan-2-yl | CH-cyclohexyl** | — | B | +41° | 273 | 18,250 | 1782 | 0.4 | 4.18 | 5.65; 8.0–9.2 |
| 16 | furan-2-yl | CHCH(CH3)2** | — | B | +69° | 273 | 18,100 | 1781 | 0.38 | 4.14 | 5.61; 5.69 |
| 17 | thien-2-yl | C(CH3)2 | — | A | +62.5° | 262 | 13,900 | 1784 | 0.37 | 4.10 | 8.51 |
| 18 | PL | C(CH3)2 | — | A | +28.6° | 257 | 15,500 | 1781 | 0.38 | 4.04 | 8.49 |

**Denotes (RS)-isomers
*Values for free acids

EXAMPLE 19

(1R,6R,7R)-3-Acetoxymethyl-7-[2-(2-carboxyprop-2-yloxyimino)-2-(fur-2-yl)acetamido]ceph-3-em-4-carboxylic acid 1-oxide (syn isomer)

(a) A solution of (6R,7R)-3-acetoxymethyl-7-[2-(2-carboxyprop-2-yloxyimino)-2-(fur-2-yl)acetamido]-ceph-3-em-4-carboxylic acid, di-t-butyl ester (syn isomer) (1.21 g) in pyridine (25 ml) and water (1 ml) at −45° was treated with t-butyl hypochlorite (0.3 ml) with vigorous stirring. After 2 minutes 2N-sulphurous acid (1 ml) was added to the solution and the mixture was immediately poured into aqueous phosphoric acid (100 ml, 20% v/v). The aqueous solution was extracted with ethyl acetate and the organic extracts were washed with 0.5N-hydrochloric acid (50 ml), aqueous sodium bicarbonate solution (50 ml) and water, then dried and concentrated in vacuo. The crude product was chromatographed on silica gel preparative plates, using ethyl acetate:petroleum ether (b.p. 60°–80°) (4:1) as eluant. The slower running band was extracted with ethyl acetate to yield the di-t-butyl ester of the title compound (505 mg); ν_max (Nujol) 1798 (β-lactam), 1738, 1727, 1715 (acetate and CO2.tBu), 1680 and 1542 cm⁻¹ (CONH); τ values (DMSO-d6) include 0.28 (d, J 8 Hz, NH), 4.19 (dd, J 5 and 8 Hz, 7-H), 5.02 (d, J 5 Hz, 6-H), 5.71 and 6.38 (ABq, J 18 Hz, 2-H).

The di-t-butyl ester (0.38 g) in trifluoroacetic acid (5 ml, containing a few drops of anisole) was stirred at room temperature for 15 minutes. The solution was concentrated in vacuo to a red oil, diluted with ethyl acetate (2 ml) and added dropwise to vigorously stirred petroleum ether (b.p. 60–80°) (50 ml). The deposited solid was collected, washed with ether (5 ml) and dried to yield the title acid (185 mg, 60%); λ_max (ethanol) 276 nm (ε 16,600); ν_max (Nujol) 1790 (β-lactam), 1730 (acetate), 1720 (CO2H), 1680 and 1523 (CONH) and 1040 cm⁻¹ (S→O); τ values (DMSO-d6) include 0.21 (d, J 8 Hz, NH), 4.17 (dd, J 5 and 8 Hz, 7-H), 5.01 (d, J 5 Hz, 6-H), 5.71 and 6.32 (ABq, J 18 Hz, 2-H), 8.49 (s, C(CH3)2).

The starting material for the above oxidation process was prepared as follows:

A solution of t-butyl (6R,7R)-7-amino-3-acetoxymethylceph-3-em-4-carboxylate (1.05 g) in dry dichloromethane (10 ml) was added to a solution of 2-(2-t-butoxycarbonylprop-2-yloxyimino)-2-(fur-2-yl)acetic acid (syn isomer) (0.99 g) and dicyclohexylcarbodiimide (0.69 g) in dry dichloromethane (10 ml), and the mixture was stirred at room temperature for 1 hour. The solution was filtered and concentrated in vacuo. The crude product was passed down a column of silica gel (MFC, 100–200 mesh, 2 × 20 cm) using ethyl acetate:petroleum ether (b.p. 60°–80° ) (1:1) as eluant. Combination of appropriate fractions as determined by thin layer chromatography yielded (6R,7R)-3-acetoxymethyl-7-[2-(2-carboxyprop-2-yloxyimino)-2-(fur-2-yl)acetamido]-ceph-3-em-4-carboxylic acid, di-t-butyl ester (syn isomer) (1.29 g); ν_max (CHBr3) 1776 (β-lactam), 1725, 1712 (acetate and CO2.tBu), 1678 and 1512 cm⁻¹ (CONH); τ (CDCl3) values include 1.90 (d, J 8 Hz, NH), 4.08 (dd, J 5 and 8 Hz, 7-H) and 4.98 (d, J 5 Hz, 6-H).

EXAMPLE A

This example illustrates the formulation of a pharmaceutical composition.

Dry Powder for Injection

Sterile (6R,7R)-3-acetoxymethyl-7-[2-(1-carboxycyclopent-1-yloxyimino)-2-(fur-2-yl)acetamido]ceph-3-em-4-carboxylate disodium salt (syn isomer) is filled into glass vials, the claimed contents of each container being 500 mg or 1.00 g of the antibiotic as desired. Filling is carried out aseptically under a blanket of nitrogen. The vials are closed using rubber discs or plugs held in position by aluminium sealing rings, thereby preventing gaseous exchange or ingress of microorganisms. The product would be intended for reconstitution with Water for Injections or other suitable sterile vehicle shortly before administration.

We claim:

1. A compound selected from the group consisting of a cephalosporin antibiotic of the formula:

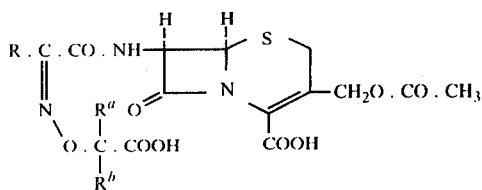

wherein

R is thienyl or furyl;

$R^a$ is methyl, ethyl, propyl, isopropyl, butyl, allyl, cyclohexyl or phenyl;

$R^b$ is hydrogen, carboxy, $C_2$–$C_5$ alkoxycarbonyl, methyl, ethyl, propyl, isopropyl, butyl, allyl, cyclohexyl or phenyl;

or $R^a$ and $R^b$ together with the carbon atom to which they are attached from a $C_{3-7}$ cycloalkylidene, group;

and a physiologically acceptable salt or 1-oxide thereof.

2. The compound of claim 1 which is (6R,7R)-3-acetoxymethyl-7-[ 2-(1-carboxycyclopent-1-yloxyimino)-2-(fur-2-yl)acetamido]ceph-3-em-4-carboxylic acid (syn isomer).

3. The compound of claim 1 which is (6R,7R)-3-acetoxymethyl-7-[2-(1-carboxybut-3-enyloxyimino)-2-(fur-2-yl)acetamido]ceph-3-em-4-carboxylic acid (syn isomer).

4. The compound of claim 1 which is (6R,7R)-3-acetoxymethyl-7-[2-(1-carboxycyclobut-1-yloxyimino)-2-(fur-2-yl)acetamido]ceph-3-em-4-carboxylic acid (syn isomer).

5. The compound of claim 1 which is (6R,7R)-3-acetoxymethyl-7-[2-(1-carboxypropoxyimino-2-(fur-2-yl)acetamido]ceph-3-em-4-carboxylic acid (syn isomer).

6. The compound of claim 1 which is (6R,7R)-3-acetoxy-methyl-7-[2-(3-carboxypent-3-yloxyimino)-2-(fur-2-yl)acetamido]ceph-3-em-4-carboxylic acid (syn isomer).

7. The compound of claim 1 which is (6R,7R)-3-acetoxy-methyl-7-[2-(2-carboxyprop-2-yloxyimino)-2-(thien-2-yl) acetamido]ceph-3-em-4-carboxylic acid (syn isomer).

8. A compound selected from the group consisting of a cephalosporin antibiotic of the formula:

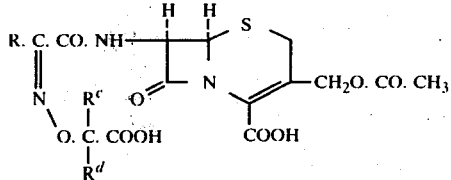

wherein R is thienyl or furyl, $R^c$ is methyl, ethyl, propyl, allyl or phenyl and $R^d$ is hydrogen, carboxy, methyl, ethyl, propyl, allyl or phenyl; or $R^c$ and $R^d$ together with the carbon atom to which they are attached form a cyclobutylidene, cyclopentylidene or cyclohexylidene group; and a physiologically acceptable salt or 1-oxide thereof.

* * * * *